United States Patent
Mohapatra et al.

(10) Patent No.: US 11,607,426 B2
(45) Date of Patent: Mar. 21, 2023

(54) METHOD OF TARGETING ONCOLYTIC VIRUSES TO TUMORS

(71) Applicants: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

(72) Inventors: Shyam S. Mohapatra, Lutz, FL (US); Subhra Mohapatra, Lutz, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 903 days.

(21) Appl. No.: 16/330,858

(22) PCT Filed: Sep. 19, 2017

(86) PCT No.: PCT/US2017/052313
§ 371 (c)(1),
(2) Date: Mar. 6, 2019

(87) PCT Pub. No.: WO2018/053529
PCT Pub. Date: Mar. 22, 2018

(65) Prior Publication Data
US 2019/0216855 A1    Jul. 18, 2019

Related U.S. Application Data

(60) Provisional application No. 62/396,604, filed on Sep. 19, 2016.

(51) Int. Cl.
| | |
|---|---|
| *A61K 35/28* | (2015.01) |
| *C12N 7/00* | (2006.01) |
| *A61P 35/00* | (2006.01) |
| *A61K 45/06* | (2006.01) |
| *C12N 5/0775* | (2010.01) |

(52) U.S. Cl.
CPC .............. *A61K 35/28* (2013.01); *A61K 45/06* (2013.01); *A61P 35/00* (2018.01); *C12N 5/0662* (2013.01); *C12N 7/00* (2013.01); *C12N 2760/18532* (2013.01); *C12N 2760/18571* (2013.01)

(58) Field of Classification Search
CPC .................................................... A61K 35/28
See application file for complete search history.

(56) References Cited

U.S. PATENT DOCUMENTS

2009/0202479 A1   8/2009 Shi et al.

FOREIGN PATENT DOCUMENTS

| WO | WO 2011/146100 | 11/2011 | |
|---|---|---|---|
| WO | WO 2014/093948 | 6/2014 | |
| WO | WO2014/160475 | * 10/2014 | ............... C12N 7/00 |
| WO | WO 2014/160475 | 10/2014 | |
| WO | WO 2015/089280 | 6/2015 | |

OTHER PUBLICATIONS

Ge et al. (Transplantation 2010;90: 1312-1320). (Year: 2010).*
Van Den Akker et al. (Osteoarthritis and Cartilage. Abstract Only, vol. 24, supplement 1, S231, Apr. 1, 2016). (Year: 2016).*
Sadhukha et al. (Journal of Controlled Release 196 (2014) 243-251) (Year: 2014).*
Gostner et al. (Expert Opinion on Therapeutic Targets, (2015) 19:5, 605-615, DOI: 10.1517/14728222.2014.995092) (Year: 2015).*
Echchgadda et al. (Cancer Gene Therapy (2009) 16, 923-935; doi:10.1038/cgt.2009.34; published online May 15, 2009). (Year: 2009).*
Ramirez et al. (Oncolytic Virotherapy 2015:4 149-155) (Year: 2015).*
NAMBA, Stem Cell-Based Gene Therapy for Malignant Gliomas, Neuro-Oncology, 2016, 23(1):21-26.
PCT International Search Report and Written Opinion, PCT/US2017/052313, dated Nov. 29, 2017, 13 pages.
European Patent Office, Examination Report, Application No. 17851803.1, dated Nov. 18, 2020, 13 pages.
European Patent Office, Examination Report, Application No. 17851803.1, dated Jun. 14, 2021, 16 pages.
Japan Patent Office, Notice of Reasons for Refusal, Application No. 2019-515539, dated Jun. 24, 2021, 11 pages.
Ajamian, F. et al. "Respiratory syncytial virus replication induces Indoleamine 2, 3-dioxygenase (IDO) activation in human dendritic cells," *Allergy, Asthma & Clinical Immunology*, 2010, pp. 1-2, vol. 6.
Bird, G.H. et al. "Mucosal delivery of a double-stapled RSV peptide prevents nasopulmonary infection," *The Journal of Clinical Investigation*, 2014, pp. 2113-2124, vol. 124, No. 5.
Boettcher, M. et al. "Choosing the Right Tool for the Job: RNAi, TALEN or CRISPR," *Mol Cell.*, 2015, pp. 575-585, vol. 58, No. 4.
Boyapalle, S. et al. "Respiratory syncytial virus NS1 protein colocalizes with mitochondrial antiviral signaling protein MAVS following infection," *PloS one*, 2012, pp. 1-9, e29386, vol. 7, No. 2.
Donnelly, O.G. et al. "Recent clinical experience with oncolytic viruses," *Current Pharmaceutical Biotechnology*, 2012, pp. 1834-1841, vol. 13, No. 9.

(Continued)

*Primary Examiner* — Scott Long
(74) *Attorney, Agent, or Firm* — Quarles & Brady LLP

(57) ABSTRACT

The present invention pertains to a strategy of selectively targeting oncolytic virotherapy, using either naturally occurring or genetically modified viruses by packaging them in mesenchymal stem cells (MSCs). The present invention concerns MSCs, compositions comprising the MSCs, and methods of using the MSCs for treatment of cancer and for lysing or inducing apoptosis of cancer cells in vitro or in vivo.

15 Claims, 7 Drawing Sheets

Specification includes a Sequence Listing.

(56) References Cited

OTHER PUBLICATIONS

Echchgadda, I. et al. "Oncolytic targeting of androgen-sensitive prostate tumor by the respiratory syncytial virus (RSV): consequences of deficient interferon-dependent antiviral defense," *BMC Cancer*, 2011, pp. 1-18 vol. 11, No. 43.
Ferguson, M.S. et al. "Systemic delivery of oncolytic viruses: hopes and hurdles," *Advances in Virology*, 2012, pp. 1-14, Article ID 805629, vol. 2012.
Guerrero-Plata, A. et al. "Activity and regulation of alpha interferon in respiratory syncytial virus and human metapneumovirus experimental infections," *Journal of Virology*, 2005, pp. 10190-10199, vol. 79, No. 16.
Hobson, L. et al. "Persistent of respiratory syncytial virus in human dendritic cells and influence of nitric oxide," *Clinical and Experimental Immunology*, 2008, pp. 359-366, vol. 151, No. 2.
Holmgaard, R.B. et al. "Indoleamine 2,3-dioxygenase is a critical resistance mechanism in antitumor T cell immunotherapy targeting CTLA-4," *The Journal of Experimental Medicine*, 2013, pp. 1389-1402, vol. 210, No. 7.
Ikeda, K. et al. "Oncolytic virus therapy of multiple tumors in the brain requires suppression of innate and elicited antiviral responses," *Nature Medicine*, 1999, pp. 881-887, vol. 5, No. 8.
Jing, W. et al. "Human umbilical cord blood-derived mesenchymal stem cells producing IL15 eradicate established pancreatic tumor in syngeneic mice," *Mol Cancer Ther*, 2014, pp. 2127-2137, vol. 13, No. 8.
Ling, W. et al. "Mesenchymal Stem Cells Use IDO to Regulate Immunity in Tumor Microenvironment," Tumor and Stem Cell Biology, *Cancer Research*, 2014, pp. 1576-1587, vol. 74, No. 5.
Moon, Y.W. et al. "Targeting the indoleamine 2,3-dioxygenase pathway in cancer," *Journal for ImmunoTherapy of Cancer*, 2015, pp. 1-10, vol. 3, No. 41.
Rezaee, F. et al. "Respiratory syncytial virus infection in human bone marrow stromal cells," *Am J Respir Cell Mol Biol*, 2011, pp. 277-286, vol. 45, No. 2.
Russell, S.J. et al. "Oncolytic virotherapy," *Nature Biotechnology*, 2012, pp. 658-670, vol. 30, No. 7.
Salimi, V. et al. "The Oncolytic Effect of Respiratory Syncytial Virus (RSV) in Human Skin Cancer Cell Line, A431," *Iranian Red Crescent Medical Journal*, 2013, pp. 62-67, vol. 15, No. 1.
Thaci, B. et al. "Pharmacokinetic study of neural stem cell-based cell carrier for oncolytic virotherapy: targeted delivery of the therapeutic payload in an orthotopic brain tumor model," *Cancer Gene Therapy*, 2012, pp. 431-442, vol. 19.
Unniyampurath, U. et al. "RNA Interference in the Age of CRISPR: Will CRISPR Interfere with RNAi?," *International Journal of Molecular Sciences*, 2016, pp. 1-15, vol. 17, No. 291.
Wong, T.M. et al. "Respiratory syncytial virus (RSV) infection in elderly mice results in altered antiviral gene expression and enhanced pathology," *PloS one*, 2014, pp. 1-18, e88764, vol. 9, No. 2.
Yeung, A.W. et al. "Role of indoleamine 2,3-dioxygenase in health and disease", *Clin. Sci.*, 2015, pp. 601-672, vol. 129, No. 7.
Zhang, W. et al. "Inhibition of respiratory syncytial virus infection with intranasal siRNA nanoparticles targeting the viral NS1 gene," *Nature Medicine*, 2005, pp. 56-62, vol. 11, No. 1.
Davis, E. "Knockout by TALEN or CRISPR vs. Knockdown by shRNA or siRNA," *GeneCopoeia™ Technical Note*, Downloaded from www.genecopoeia.com on Sep. 19, 2017.
Mohapatra, S. et al. "Tumor targeted engineered stem cells for treatment of lung cancer" Oct. 1, 2017, *National Institutes of Health*, Retrieved from the internet on Feb. 14, 2020: URL:http://grantome.com/grant/NIH/I01-BX003413-01A2, pp. 1-3.
Cheung, M.B. et al., "Respiratory Syncytial Virus-Infected Mesenchymal Stem Cells Regulate Immunity via Interferon Beta and Indoleamine-2,3-Dioxygenase" *PLOS ONE*, Oct. 3, 2016, pp. 1-27, vol. 11, No. 10.
Ge, W. et al., "Regulatory T-Cell Generation and Kidney Allograft Tolerance Induced by Mesenchymal Stem Cells Associated With Indoleamine 2,3-Dioxygenase Expression" *Transplantation*, Dec. 27, 2010, pp. 1312-1320, vol. 90, No. 12.
Ong, H.T. et al., "Systemically delivered measles virus-infected mesenchymal stem cells can evade host immunity to inhibit liver cancer growth" *Journal of Hepatology*, Jul. 16, 2013, pp. 999-1006, vol. 59.
Echchgadda, I. et al., "Anticancer oncolytic activity of respiratory syncytial virus" *Cancer Gene Therapy*, May 15, 2009, pp. 923-935, vol. 16.
Cheung, M.B. et al., "Respiratory Syncytial Virus (RSV) Infection and Replication in Mesenchymal Stem Cells (MSCs)" *Journal of Allergy and Clinical Immunology*, Feb. 1, 2013, pp. AB74, vol. 131, No. 2.
Qiao, J. et al., "Intratumoral oncolytic adenoviral treatment modulates the glioma microenvironment and facilitates systemic tumor-antigen-specific T cell therapy" *OncoImmunology*, Apr. 2, 2015, pp. e1022302-1-e1022302-11, vol. 4, No. 8.
European Search Report issued by the European Patent Office dated Mar. 17, 2020 for Application No. 17851803.1, pp. 1-16.

\* cited by examiner

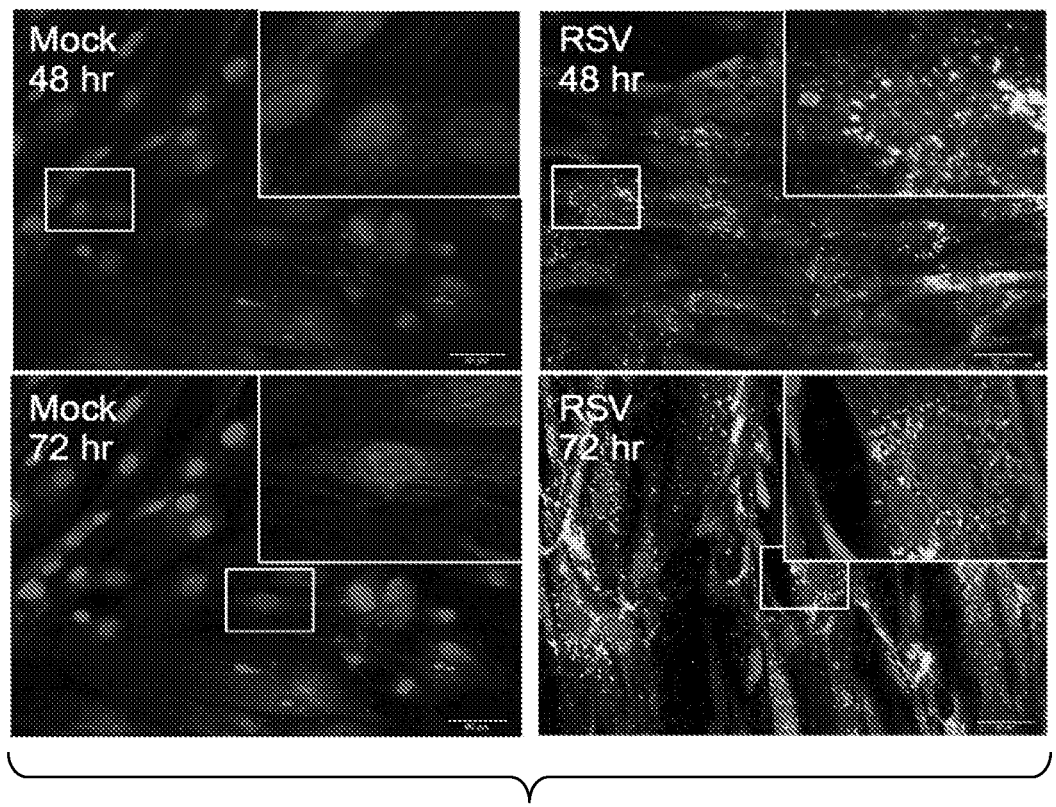
FIG. 1A
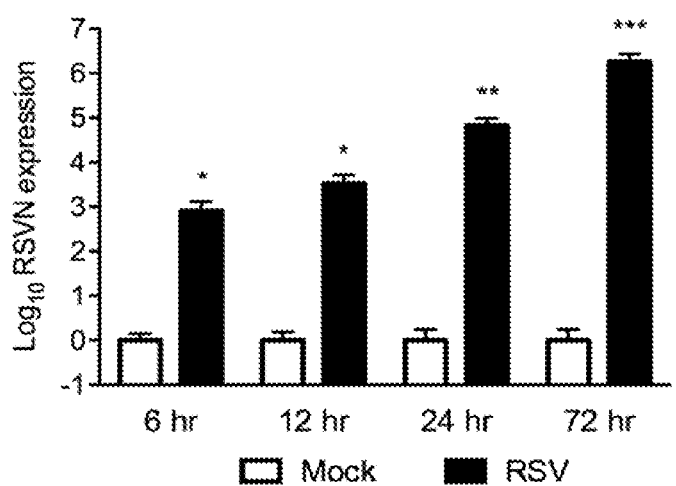 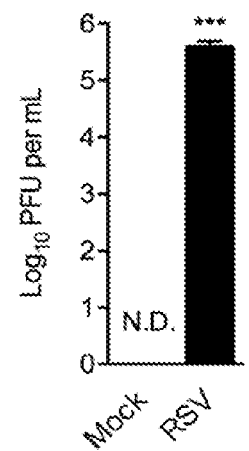
FIG. 1B      FIG. 1C

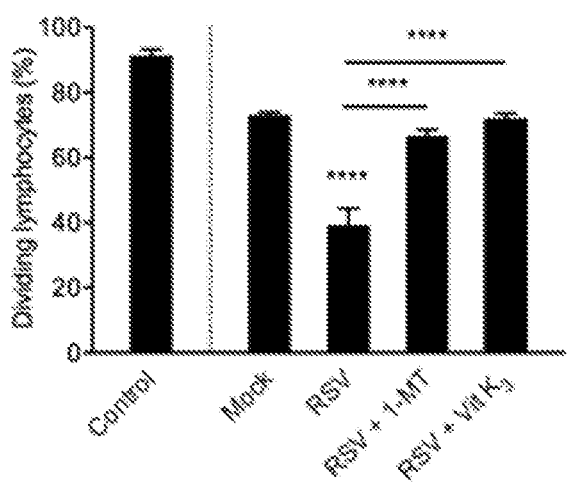
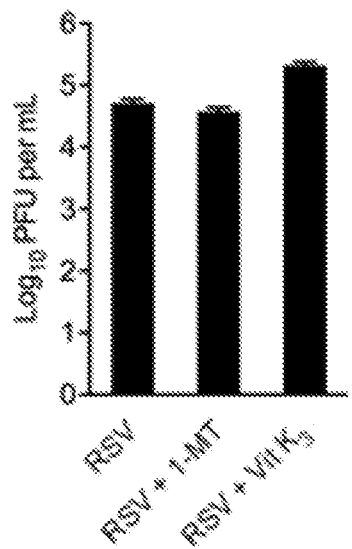
FIG. 2A  FIG. 2B
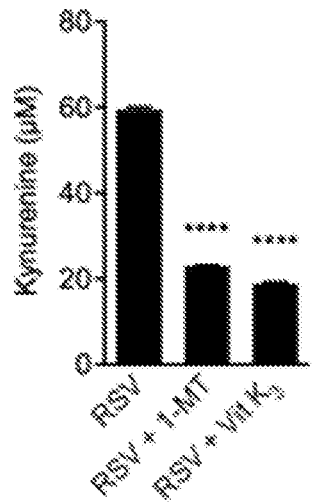
FIG. 2C

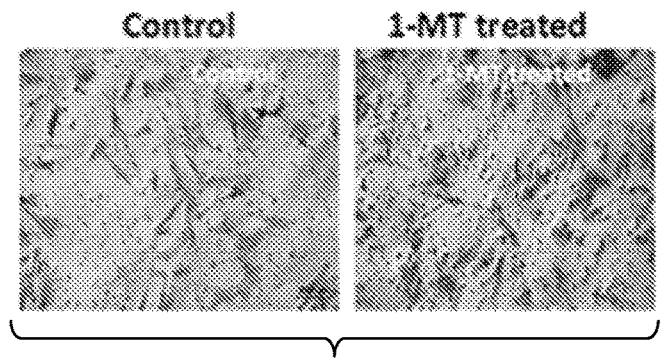
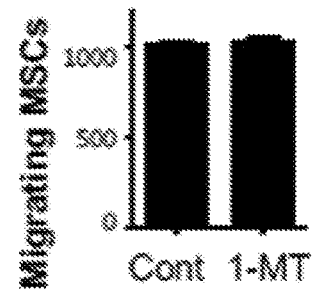
FIG. 4A  FIG. 4B
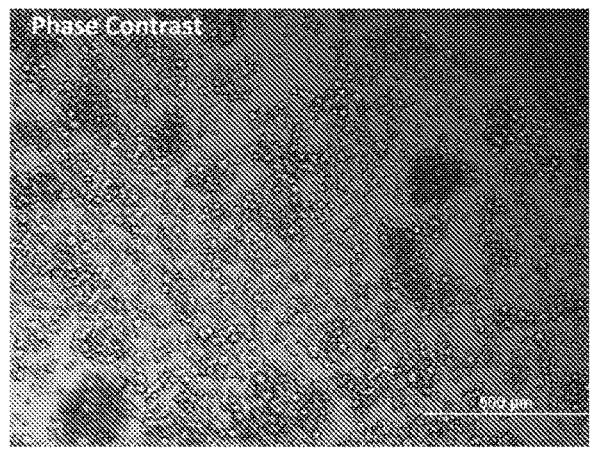
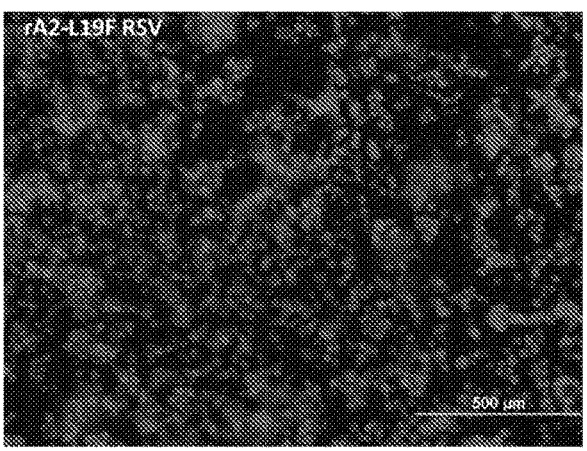
FIG. 5A-1  FIG. 5A-2
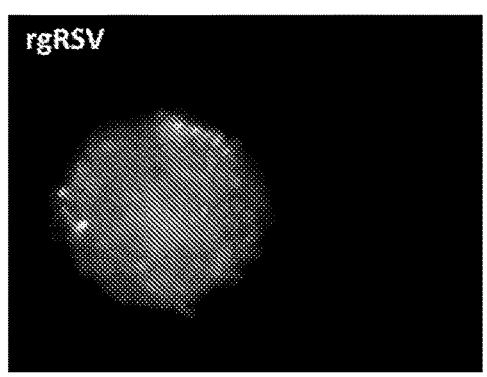
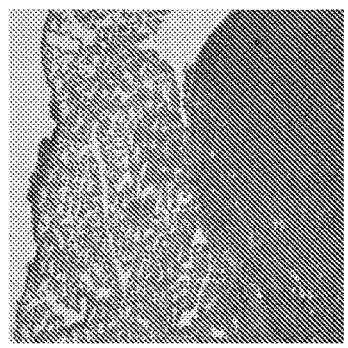
FIG. 5B  FIG. 5C

SEQUENCE LISTING

```
<160> NUMBER OF SEQ ID NOS: 2

<210> SEQ ID NO 1
<211> LENGTH: 403
<212> TYPE: PRT
<213> ORGANISM: Homo sapiens

<400> SEQUENCE: 1

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160
```

```
Lys Gly Phe Phe Leu Val Ser Leu Leu Val Glu Ile Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
            195                 200                 205

Lys Ala Leu Gln Val Phe His Gln Ile His Asp His Val Asn Pro Lys
            210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
                260                 265                 270

Phe Asp Val Leu Leu Gly Ile Gln Gln Thr Ala Gly Gly Gly His Ala
                275                 280                 285

Ala Gln Phe Leu Gln Asp Met Arg Arg Tyr Met Pro Pro Ala His Arg
            290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
                355                 360                 365

Glu Asp Pro Ser Lys Leu Glu Ala Lys Gly Thr Gly Thr Asp Leu
            370                 375                 380

Met Asn Phe Leu Lys Thr Val Arg Ser Thr Thr Glu Lys Ser Leu Leu
385                 390                 395                 400

Lys Glu Gly

<210> SEQ ID NO 2
<211> LENGTH: 1944
<212> TYPE: DNA
<213> ORGANISM: Homo sapiens

<400> SEQUENCE: 2
aatttctcac tgcccctgtg ataaactgtg gtcactggct gtggcagcaa ctattataag      60
atgctctgaa aactcttcag acactgaggg gcaccagagg agcagactac aagaatggca     120
cacgctatgg aaaactcctg acaatcagt aaagagtacc atattgatga agaagtgggc      180
tttgctctgc caaatccaca ggaaaatcta cctgattttt ataatgactg gatgttcatt     240
gctaaacatc tgcctgatct catagagtct ggccagcttc gagaaagagt tgagaagtta     300
aacatgctca gcattgatca tctcacagac acaagtcac agcgccttgc acgtctagtt     360
ctgggatgca tcaccatggc atatgtgtgg ggcaaaggtc atggagatgt ccgtaaggtc     420
ttgccaagaa atattgctgt tccttactgc caactctcca agaaactgga actgcctcct     480
attttggttt atgcagactg tgtcttggca aactggaaga aaaaggatcc taataagccc     540
ctgacttatg agaacatgga cgttttgttc tcatttcgtg atggagactg cagtaaagga     600
ttcttcctgg tctctctatt ggtggaaata gcagctgctt ctgcaatcaa gtaattcct      660 actgtattca aggcaatgca aatgcaagaa cgggacactt tgctaaaggc gctgttggaa     720
```

```
atagcttctt gcttggagaa agcccttcaa gtgtttcacc aaatccacga tcatgtgaac    780
ccaaaagcat ttttcagtgt tcttcgcata tatttgtctg gctggaaagg caacccccag    840
ctatcagacg gtctggtgta tgaagggttc tgggaagacc caaggagtt tgcagggggc     900 agtgcaggcc aaagcagcgt ctttcagtgc tttgacgtcc tgctgggcat ccagcagact    960
gctggtggag gacatgctgc tcagttcctc caggacatga gaagatatat gccaccagct   1020
cacaggaact tcctgtgctc attagagtca aatccctcag tccgtgagtt tgtcctttca   1080
aaaggtgatg ctggcctgcg ggaagcttat gacgcctgtg tgaaagctct ggtctccctg   1140
aggagctacc atctgcaaat cgtgactaag tacatcctga ttcctgcaag ccagcagcca   1200
aaggagaata agacctctga agacccttca aaactggaag ccaaaggaac tggaggcact   1260
gatttaatga atttcctgaa gactgtaaga agtacaactg agaaatccct tttgaaggaa   1320
ggttaatgta acccaacaag agcacatttt atcatagcag agacatctgt atgcattcct   1380
gtcattaccc attgtaacag agccacaaac taatactatg caatgtttta ccaataatgc   1440
aatacaaaag acctcaaaat acctgtgcat ttcttgtagg aaaacaacaa aaggtaatta   1500
tgtgtaatta tactagaagt tttgtaatct gtatcttatc attggaataa aatgacattc   1560
aataaataaa aatgcataag atatattctg tcggctgggc gcggtggctc acgcctgtaa   1620
tcccagcact ttgggaggcc gaggcgggcg gatcacaagg tcaggagatc gagaccatct   1680
tggctaacac ggtgaaaccc cgtctctact aaaaatacaa aaaattagcc gggcgcggtg   1740
gcgggcacct gtagtcccag ctactcggga ggctgaggca ggagaatggc gtgaacctgg   1800
gaggcggagc ttgcagtgag ccaagattgt gccactgcaa tccggcctgg gctaaagagc   1860
gggactccgt ctcaaaaaaa aaaaaaaaaa gatatattct gtcataataa ataaaaatgc   1920
ataagatata aaaaaaaaaa aaaa                                          1944
```

METHOD OF TARGETING ONCOLYTIC VIRUSES TO TUMORS

CROSS-REFERENCE TO RELATED APPLICATIONS

The present application is the National Stage of International Application No. PCT/US2017/052313, filed Sep. 19, 2017, which claims the benefit of U.S. Provisional Application Ser. No. 62/396,604, filed Sep. 19, 2016, each of which is hereby incorporated by reference herein in its entirety, including any figures, tables, nucleic acid sequences, amino acid sequences, or drawings.

BACKGROUND OF THE INVENTION

Lung cancers remain the leading cause worldwide of cancer-related mortality in both men and women (National Comprehensive Cancer Network). Deaths due to lung cancers exceed the combined number of deaths from the leading types of carcinoma (breast, prostate and colon cancer), and account for 6% of all deaths within the US (1). Lung cancer patients often present with locally advanced or disseminated disease. Such aggressive lung cancers are difficult to treat due to drug-induced toxicity, as a result ~6 out of 10 people die within one year of diagnosis. Available treatment options have limited therapeutic success in non-small cell lung cancer (NSCLC), constituting ~85% of all lung cancer patients, as it becomes resistant to therapy. This is partly due to the tumor itself, a heterogeneous mixture of cells depending on different survival pathways. This heterogeneity allows some of the drug-sensitive cancer cells to eventually acquire resistance to treatment. Radiotherapy, alone or in combination with surgery or chemotherapy, is useful in the management of NSCLC (2). Radiotherapy can be problematic for NSCLC treatment due to tumor radio-resistance before treatment and acquired radio-resistance during radiotherapy, which has been linked with specific genes, such as p53 (3), EGFR (4), and TNNC1 (calcium signaling pathway) (5). Thus, despite progress in surgery, chemotherapy, radiation therapy and development of tumor-specific monoclonal antibodies, advanced or metastatic NSCLC remains difficult-to-treat (6). Such development of resistance to classical chemo- and radio-therapies, underscore the need for development of novel, non-palliative therapeutic strategies.

These challenges have led to the re-emergence of oncolytic viro-therapy (7), a strategy using either naturally occurring or genetically modified viruses to selectively target and lyse tumor cells or kill them by apoptosis while leaving surrounding non-malignant cells unharmed. Despite clinical trials with a few viruses that showed promise in terms of safety and tolerability (8), there remain formidable challenges (9), which include: 1) the vulnerability of viruses to host immune system including complements, neutralizing Abs and macrophages, which rapidly clears the virus from circulation (10); 2) non-specific uptake by other tissues, e.g., by spleen and liver and suboptimal viral escape from the vascular compartment decreases virus reaching the tumor target (9); and 3) targeting the virus specifically to tumor, not healthy tissue. Particularly, for lung cancers, the development of oncolytic virotherapy has been very limited. Also, targeting oncolytic viruses to tumors and tumor cells in the lung remains a major unmet need.

BRIEF SUMMARY OF THE INVENTION

The present invention pertains to a strategy of selectively targeting oncolytic virotherapy, using either naturally occurring or genetically modified viruses by packaging them in mesenchymal stem cells (MSCs), such as human MSCs (hMSCs). Such tumoritropic targeting of the virus, specifically lyse tumor cells or kill them by apoptosis, while leaving surrounding non-malignant cells unharmed. In one embodiment of the invention, hMSCs were found to be almost 100% infected by respiratory syncytial virus (RSV) in cultures. However, such infection also increased the expression of IDO, that inhibits anti-tumor immunity, which is known to have immunosuppressive property. In another embodiment, hMSCs rendered IDO-negative using the CRISP/R method lost their immunosuppressive function. These IDO-deficient hMSCs were found to be capable of being infected by RSV and the infected cells retained their ability to migrate to the tumor sites. In another embodiment, RSV was shown to infect lung cancer cells such as the LLC1 cells in both monolayer and tumoroid cultures.

One aspect of the invention concerns a mesenchymal stem cell (MSC) that is: (a) infected with a naturally occurring or genetically modified oncolytic virus, or (b) is indoleamine 2,3-dioxygenase (IDO)-deficient, or both (a) and (b).

Another aspect of the invention concerns a composition comprising an MSC as described herein, and a pharmaceutically acceptable carrier or diluent, which is useful for the treatment of cancer. Optionally, the composition may include one or more adjuvants.

Another aspect of the invention concerns a method for treating cancer, comprising administering an effective amount of the MSCs described herein to a human or non-human animal subject in need thereof.

Another aspect of the invention concerns a method for lysing or inducing apoptosis of cancer cells in vitro or in vivo, comprising contacting the cancer cells in vitro or in vivo with, or bringing into close proximity, an effective amount of MSC as described herein.

Another aspect of the invention concerns a method for producing an oncolytic agent, comprising: providing an MSC; and infecting the MSC with an oncolytic virus. Optionally, the infected MSC may be combined as a composition with a pharmaceutically acceptable carrier or diluent. Optionally, the composition may include one or more adjuvants.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 1A-1E. RSV infects and replicates in hMSCs. (1A) hMSCs were infected with RSV (MOI=1), immunostained at 48 or 72 h p.i. with a mAb to GFP-RSV, Evan's blue dye (red) and DAPI (blue) and visualized by confocal microscopy (mag 200× or 1000×). (1B) RSV nucleocapsid (RSVN) transcripts detected in MSCs at 6, 12, 24 and 72 hours p.i. normalized to mock. (1C) RSV titers (PFU/ml) isolated from the culture medium of infected MSCs. Results representative of at least duplicate experiments. *p<0.05, p<0.01, *p<0.001. qPCR analysis of interferon-β (1D) and IDO (1E) expression in RSV-infected NHBE and MSCs compared to mock-infected cells (n=6) by 72 h p.i., *p<0.05, **p<0.01.

FIGS. 2A-2F: (2A) IDO antagonists abrogate proliferative inhibition by RSV-infected MSC CM. CFSE labeled PBMCs were treated with CM from uninfected (mock) or RSV-infected hMSC cultures in the presence or absence of 1 mM 1-MT and 10 μM of vitamin K3 cultured (triplicate) for 5 days with the mitogen PHA. Cell proliferation analyzed by flow cytometry. (2B-2C) RSV infection (2B) and kynurenine levels (2C) in 1-MT or vitamin $K_3$ treated human MSCs. (2D-2F) RSV infection in IDO-deficient mice. Wild type and IDO-knockout mice were infected intranasally with $3 \times 10^6$ pfu RSV, euthanized 5 days p.i. and lungs were examined for RSV infection (2D), RSVN- (2E) and IFN-β-(2F) transcripts by qPCR. $*p<0.05$, $*p<0.001$ & $p<0.0001$

FIGS. 4A-4B: LLC1 tumoroids were cultured with hMSCs in the presence or absence of 1MT in transwell insert. Migrated MSCs were counted after 24 h. Each group was done in triplicates. (4A) Representative images and (4B) means±SD of migrated MSCs are shown.

FIGS. 5A-1, 5A-2, 5B, 5C, 5D, 5E, 5F: Susceptibility of LLC1 monolayer (5A-1 and 5A-2) and tumoroids (5B) to RSV infection. A representative picture is shown. (5C) Establishment of orthotopic lung tumors. After incision of the skin overlying the left chest wall in the mid-axillary line, LLC1 (~$10^6$ cells/mouse) cells were injected into the left lung. Two weeks after inoculation, lungs were harvested, fixed and sectioned H&E stained. (5D) Tumor tropism of hMSC. I.V. administered PKH26-labeled hMSC to tumor bearing GFP-C57BL/6 mouse lungs (left) detected by IVIS imaging, 24 hrs post injection. Right: control tumor bearing GFP-C57BL/6 mouse. (5E-5F) RSV detection in mouse lung tumors 5 days post infection of RSV-loaded hMSC via i.n. route. (5E) Immunostaining with a anti-RSV antibody (Abcam), (5F) RSV N transcripts by q-PCR $*p<0.05$.

BRIEF DESCRIPTION OF THE SEQUENCES

Figure 1D:
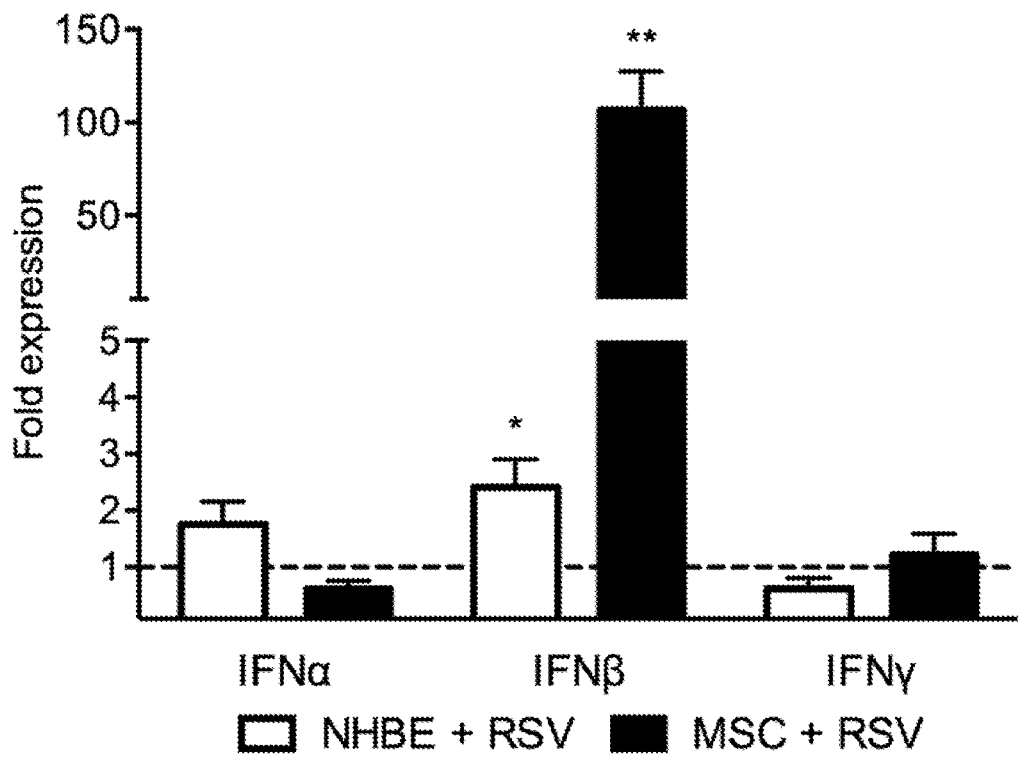

SEQ ID NO:1—Human IDO amino acid sequence (UniProt accession number P14902).
SEQ ID NO:2—Human IDO nucleic acid sequence (NCBI Accession number NM_ 002164, version NM_002164.5).

DETAILED DESCRIPTION OF THE INVENTION

The inventors have extensively studied RSV for the last decade in relation to its immunobiology and its interaction with diverse host cells including A549 lung carcinoma epithelial cells and normal human bronchial epithelial cells (NHBE) (11-14) and have shown that RSV-induced IFN-β to be important to apoptosis. Wild-type (wt) RSV was shown to be oncolytic when delivered locally to prostate cancer xenograft tumors (15); however, it cannot be given locally to all tumors. Thus, there is a need to administer viruses systemically, and to target the virus to the tumors. Also, the inventors found that lung cancer cells did not show a cytopathic effect (CPE) when infected with wt-RSV presumably because RSV primarily infects cells that are poor producers of IFN-β, e.g., NHBE cells (16).

Although RSV commonly infects the apical airway epithelial cells, only about 40% of cells in a culture get infected. An error in cell handling in the inventors' lab led to the finding that human MSCs (hMSCs) are highly susceptible to RSV. Since MSCs are known to target to tumors (17), the inventors hypothesized that RSV-infected hMSCs might be useful to develop targeted oncolytic virotherapy. However, initial studies showed that RSV-infected hMSCs upregulate IDO expression and activity, which could suppress anti-tumor immunity. Thus, the inventors produced IDO-negative MSCs, which provide targeted delivery of RSV-based oncolytic therapy, and which may be used to deliver other oncolytic virotherapies.

The MSC may be a human MSC or a non-human animal MSC. In some embodiments, the subject receiving the MSC is human and the MSC is a human MSC.

The MSC may be autologous, allogeneic, or xenogeneic to the subject to which the MSCs are administered.

The oncolytic virus should be oncolytic for the cancer cell type. Examples of oncolytic viruses include, but are not limited to, respiratory syncytial virus (RSV), herpes simplex virus, vesicular stomatitis virus, poliovirus, reovirus, senecavirus, and RIGVIR. In some embodiments, the virus is RSV. In some embodiments, the virus is RSV and the cancer is lung cancer.

The virus may be engineered or genetically modified, for example, by attenuation (e.g., deleting viral genes or gene regions to eliminate viral functions that are expendable in tumor cells, but not in normal cells, thus making the virus safer and more tumor-specific); tumor targeting (e.g., transductional targeting or non-transductional targeting); inclusion of reporter genes (e.g., green fluorescent protein (GFP)); improvement of oncolytic activity (e.g., inclusion of suicide genes, suppression of angiogenesis by addition of anti-angiogenic genes, radioiodine (accumulation of iodine by addition of the sodium-iodide symporter (NIS) gene)).

The MSCs may be administered to the subject, or brought into contact or proximity to the target cancer cells in vitro or in vivo, in an isolated state and, optionally, combined with a pharmaceutically acceptable carrier or diluent, as a pharmaceutical composition. Optionally, the composition can further include one or more additional biologically active agents, such as an adjuvant, chemotherapeutic, immunotherapeutic, etc.

Optionally, MSCs can be co-administered, simultaneously or consecutively, with one or more other agents to a subject. Anti-cancer agents that may be administered include but are not limited to those listed Table 1.

Co-administration can be carried out simultaneously (in the same or separate formulations) or consecutively with the additional agent administered before and/or after one or more compounds disclosed herein.

Thus, the MSCs, whether administered separately, or as a pharmaceutical composition, can include various other components. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the MSCs, or act towards preventing any potential side effects which may be posed as a result of administration of the MSCs or other agents.

In some embodiments, the compositions of the invention include at least one additional anti-cancer agent (e.g., a chemotherapeutic agent). In some embodiments of the methods of the invention, at least one additional anti-cancer agent is administered with the MSCs.

In some embodiments, the compositions can include, and the methods can include administration of, one or more proteasome inhibitors (e.g., bortezomib), inhibitors of autophagy (e.g., chloroquine), alkylating agents (e.g., melphalan, cyclophosphamide), MEK inhibitors (e.g., PD98509), FAK/PYK2 inhibitors (e.g., PF562271), or EGFR inhibitors (e.g., erlotinib, gefitinib, cetuximab, panitumumab, zalutumumab, nimotuzumab, matuzumab), or a combination of two or more of the foregoing.

Thus, immunotherapeutics, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the MSCs or other agents, or act towards preventing any potential side effects which may be posed as a result of administration of the MSCs or other agents. The immunotherapeutic agent can be conjugated to a therapeutic agent or other agent, as well.

As used herein, the term "immunotherapy" refers to the treatment of disease via the stimulation, induction, subversion, mimicry, enhancement, augmentation or any other modulation of a subject's immune system to elicit or amplify adaptive or innate immunity (actively or passively) against cancerous or otherwise harmful proteins, cells or tissues. Immunotherapies (i.e., immunotherapeutic agents) include cancer vaccines, immunomodulators, monoclonal antibodies (e.g., humanized monoclonal antibodies), immunostimulants, dendritic cells, and viral therapies, whether designed to treat existing cancers or prevent the development of cancers or for use in the adjuvant setting to reduce likelihood of recurrence of cancer. Examples of cancer vaccines include GVAX, Stimuvax, DCVax and other vaccines designed to elicit immune responses to tumor and other antigens including MUC1, NY-ESO-1, MAGE, p53 and others. Examples of immunomodulators include 1MT, Ipilimumab, Tremelimumab and/or any drug designed to de-repress or otherwise modulate cytotoxic or other T cell activity against tumor or other antigens, including, but not restricted to, treatments that modulate T-Reg cell control pathways via CTLA-4, CD80, CD86, MHC, B7-DC, B7-H1, B7-H2, B7-H3, B7-H4, CD28, other TCRs, PD-1, PDL-1, CD80, ICOS and their ligands, whether via blockade, agonist or antagonist. Examples of immunostimulants include corticosteroids and any other anti- or pro-inflammatory agent, steroidal or non-steroidal, including, but not restricted to, GM-CSF, interleukins (e.g., IL-2, IL-7, IL-12), cytokines such as the interferons, and others. Examples of dendritic cell (DC) therapies include modified dendritic cells and any other antigen presenting cell, autologous or xeno, whether modified by multiple antigens, whole cancer cells, single antigens, by mRNA, phage display or any other modification, including but not restricted to ex vivo-generated, antigen-loaded dendritic cells (DCs) to induce antigen-specific T-cell immunity, ex vivo gene-loaded DCs to induce humoral immunity, ex vivo-generated antigen-loaded DCs induce tumour-specific immunity, ex vivo-generated immature DCs to induce tolerance, including but not limited to Provenge and others. Examples of viral therapies include oncolytic viruses or virus-derived genetic or other material designed to elicit anti-tumor immunity and inhibitors of infectious viruses associated with tumor development, such as drugs in the Prophage series. Examples of monoclonal antibodies include Alemtuzumab, Bevacizumab, Cetuximab, Gemtuzumab ozogamicin, Rituximab, Trastuzumab, Radioimmunotherapy, Ibritumomab tiuxetan, Tositumomab/iodine tositumomab regimen. An immunotherapy may be a monotherapy or used in combination with one or more other therapies (one or more other immunotherapies or non-immunotherapies).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of anti-cancer agents, including chemotherapeutic agents, that may be used in conjunction with the compositions and methods of the invention are listed in Table 1. In some embodiments, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 1

Examples of Anti-Cancer Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6 - TG | Nilutamide |
| 6 - Thioguanine | Nitrogen Mustard |
| 6-Mercaptopurine | Novaldex |

TABLE 1-continued

Examples of Anti-Cancer Agents

| | |
|---|---|
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin | Viadur |
| hydrochloride | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL - 2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin - 2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |

TABLE 1-continued

Examples of Anti-Cancer Agents

| | |
|---|---|
| Mesnex | Lanacort |
| Methotrexate | L-asparaginase |
| Methotrexate Sodium | LCR |
| Methylprednisolone | |

One or more adjuvants may be administered with the MSCs, within the same composition as the MSCs, or in a separate composition before, during, and/or after administration of the MSCs. The adjuvant may be of any class such as alum salts and other mineral adjuvants, bacterial, products or bacteria-derived adjuvants, tensoactive agents (e.g., saponins), oil-in-water (o/w) and water-in-oil (w/o) emulsions, liposome adjuvants, cytokines (e.g., IL-2, GM-CSP, IL-12, and IFNgamma), and alpha-galactosylceramide analogs. Nonlimiting examples of adjuvants include Montanide emulsions, QS21, Freund's complete or incomplete adjuvant, aluminum phosphate, aluminum hydroxide, Bacillus Calmette-Guerin (BCG), and alum.

The MSCs may be administered in a composition that is adapted for an appropriate route of administration, such as enteral, parenteral, intravenous, intramuscular, topical, subcutaneous, and so forth. The MSCs can be administered at continuous or at distinct intervals, as can be determined by a person of ordinary skill in the art.

In some embodiments, the MSCs are administered to the subject systemically. In some embodiments, the MSCs are administered to the subject at an anatomical location remote from the site of a cancer. In some embodiments, the MSCs are administered locally, at the site of a cancer. In some embodiments, the MSCs are administered intranasally. In some embodiments, the MSCs are administered intravascularly (e.g., intravenously).

Various methods may be used to induce transient or sustained indoleamine 2,3-dioxygenase (IDO)-deficiency in the MSC. For example, gene deletion or gene silencing may be used to eliminate or reduce IDO expression in the MSC before, during, or after, infection with the oncolytic virus, such as homologous recombination, RNA interference (RNAi), transcription activator-like effector nucleases (TALENs), and Clustered Regularly Interspaced Short Palindromic Repeats (CRISPR) mechanism (see, for example, (22), (23), and (24), which are each incorporated herein by reference in their entireties. In some embodiments, a CRISPR/Cas9 system is used (see Example 3). The deficiency in IDO function and/or expression may be complete (100%) or partial (e.g., 90%, 80%, 70%, 60%, 50%).

The nucleic acid and amino acid sequences of human IDO are known (NCBI accession number NM_002164, version NM_002164.5 GI:323668304; UniProt accession number P14902, which are incorporated herein by reference in their entirety).

-Human IDO amino acid sequence:

SEQ ID NO: 1

MAHAMENSWTISKEYHIDEEVGFALPNPQENLPDFYNDWMFIAKHLPDLIESGQL

RERVEKLNMLSIDHLTDHKSQRLARLVLGCITMAYVWGKGHGDVRKVLPRNIA

VPYCQLSKKLELPPILVYADCVLANWKKKDPNKPLTYENMDVLFSFRDGDCSKG

FFLVSLLVEIAAASAIKVIPTVFKAMQMQERDTLLKALLEIASCLEKALQVFHQIH

DHVNPKAFFSVLRIYLSGWKGNPQLSDGLVYEGFWEDPKEFAGGSAGQSSVFQC

FDVLLGIQQTAGGGHAAQFLQDMRRYMPPAHRNFLCSLESNPSVREFVLSKGDA

GLREAYDACVKALVSLRSYHLQIVTKYILIPASQQPKENKTSEDPSKLEAKGTGG

TDLMNFLKTVRSTTEKSLLKEG (UniProt accession number P14902)

-Human IDO nucleic acid sequence:

SEQ ID NO: 2

```
  1    aatttctcac tgcccctgtg ataaactgtg gtcactggct gtggcagcaa ctattataag
 61    atgctctgaa aactcttcag acactgaggg gcaccagagg agcagactac aagaatggca
121    cacgctatgg aaaactcctg gacaatcagt aaagagtacc atattgatga agaagtgggc
181    tttgctctgc caaatccaca ggaaaatcta cctgattttt ataatgactg gatgttcatt
241    gctaaacatc tgcctgatct catagagtct ggccagcttc gagaaagagt tgagaagtta
301    aacatgctca gcattgatca tctcacagac cacaagtcac agcgccttgc acgtctagtt
361    ctgggatgca tcaccatggc atatgtgtgg ggcaaaggtc atggagatgt ccgtaaggtc
421    ttgccaagaa atattgctgt tccttactgc caactctcca agaaactgga actgcctcct
481    attttggttt atgcagactg tgtcttggca aactggaaga aaaaggatcc taataagccc
541    ctgacttatg agaacatgga cgttttgttc tcatttcgtg atggagactg cagtaaagga
601    ttcttcctgg tctctctatt ggtggaaata gcagctgctt ctgcaatcaa agtaattcct
661    actgtattca aggcaatgca aatgcaagaa cgggacactt tgctaaaggc gctgttggaa
721    atagcttctt gcttggagaa agcccttcaa gtgtttcacc aaatccacga tcatgtgaac
```

```
781   ccaaaagcat tttcagtgt tcttcgcata tatttgtctg gctggaaagg caacccccag 841   ctatcagacg gtctggtgta tgaagggttc tgggaagacc caaaggagtt tgcagggggc 901   agtgcaggcc aaagcagcgt ctttcagtgc tttgacgtcc tgctgggcat ccagcagact 961   gctggtggag gacatgctgc tcagttcctc caggacatga gaagatatat gccaccagct 1021  cacaggaact tcctgtgctc attagagtca aatccctcag tccgtgagtt tgtcctttca 1081  aaaggtgatg ctggcctgcg ggaagcttat gacgcctgtg tgaaagctct ggtctccctg 1141  aggagctacc atctgcaaat cgtgactaag tacatcctga ttcctgcaag ccagcagcca 1201  aaggagaata agacctctga agacccttca aaactggaag ccaaaggaac tggaggcact 1261  gatttaatga atttcctgaa gactgtaaga agtacaactg agaaatccct tttgaaggaa 1321  ggttaatgta acccaacaag agcacatttt atcatagcag agacatctgt atgcattcct 1381  gtcattaccc attgtaacag agccacaaac taatactatg caatgtttta ccaataatgc 1441  aatacaaaag acctcaaaat acctgtgcat ttcttgtagg aaaacaacaa aaggtaatta 1501  tgtgtaatta tactagaagt tttgtaatct gtatcttatc attggaataa aatgacattc 1561  aataaataaa aatgcataag atatattctg tcggctgggc gcggtggctc acgcctgtaa 1621  tcccagcact ttgggaggcc gaggcgggcg gatcacaagg tcaggagatc gagaccatct 1681  tggctaacac ggtgaaaccc cgtctctact aaaaatacaa aaaattagcc gggcgcggtg 1741  gcgggcacct gtagtcccag ctactcggga ggctgaggca ggagaatggc gtgaacctgg 1801  gaggcggagc ttgcagtgag ccaagattgt gccactgcaa tccggcctgg gctaaagagc 1861  gggactccgt ctcaaaaaaa aaaaaaaaaa gatatattct gtcataataa ataaaaatgc 1921  ataagatata aaaaaaaaaa aaaa
```

(NCBI Accession number NM_002164, version NM_002164.5 GI:323668304; Yeung Aw et al., "Role of indoleamine 2,3-dioxygenase in health and disease", Clin. Sci. 129 (7), 601-672 (2015), which is incorporated herein by reference in its entirety).

As indicated above, initial studies showed that RSV-infected MSCs upregulate IDO expression and activity, which could potentially have the undesisirable effect of suppressing anti-tumor immunity. One approach to avoid this is to use IDO-deficient MSCs, as described above. Another approach is to utilize inhibitors of indoleamine 2,3-dioxygenase (IDO inhibitors). Optionally, one or more IDO inhibitors may be administered to the subject, or brought into contact or proximity to the target cancer cells in vitro or in vivo. IDO inhibitors may be administered by appropriates routes of administration, such as enteral, parenteral, intravenous, intramuscular, topical, subcutaneous, and so forth. Administration can be continuous or at distinct intervals, as can be determined by a person of ordinary skill in the art. IDO inhibitors may be administered to a subject within the same composition as the MSCs, or administered in a separate composition before, during, or after administration of the MSCs.

The IDO inhibitors may be administered to the subject with MSCs having normal IDO function, or the IDO inhibitors may be administered with IDO-deficient MSCs in order to inhibit IDO endogenously. IDO is an immunoregulatory enzyme that suppresses T-cell responses and promotes immune tolerance. IDO catabolizes tryptophan and is believed to help tumor cells escape the immune system at least in part by depleting Trp in the tumor microenvironment. IDO helps create a tolerogenic milieu within the tumor and the associated tumor-draining lymph nodes. IDO directly suppresses the proliferation and differentiation of effector T cells, and markedly enhances the suppressor activity of Tregs. IDO inhibitors include, for example, hydroxyamidines such as INCB023843 and INCB024360 (WO 2006122150) and tryptophan analogs such as 1-methyl tryptophan, dextro-1-methyl tryptophan (D-1MT). Other IDO inhibitors are described in WO2014159248, US20120277217, US20140315962, and US20140323740, which are incorporated herein by reference in their entireties.

The IDO inhibitor may have one or more mechanisms of action ((21); the contents of which is incorporated herein by reference in its entirety). The IDO inhibitor may be an IDO1 inhibitor, an IDO2 inhibitor, or both. The IDO inhibitor may be any class of molecule, such as a small molecule or a biologic such as a nucleic acid (such as interfering RNA specific for IDO 1 and/or IDO2), protein or peptide, antibody or antibody fragment. Examples of IDO inhibitors include, but are not limited to, D-1MT (a tryptophan mimetic, D isoform of MT; and transcriptional suppressor of IDO), L-1MT (a tryptophan mimetic, L isoform of MT, and selective IDO1 inhibitor), MTH-Trp (tryptophan mimetic and transcriptional suppressor of IDO), β-carbolines (a tryptophan mimetic, and IDO and TDO inhibitor), Naphthoquinone-based inhibitor (a pharmacophore of natural product annulin B; indole mimetic; and an IDO inhibitor), S-allyl-brassinin (a phytoalexin and indole mimetic), S-benzyl-brassinin (a phytoalexin and indole mimetic), 5-Bromo-brassinin (a phytoalexin and indole mimetic), phenylimidazole-based inhibitor (a computationally designed synthetic IDO inhibitor), 4-phenylimidazole (a heme ligand in IDO enzyme), Exiguamine A (a non-tryptophan analogue, and NSC401366 a (a non-indolic IDO inhibitor). IDO inhibitors undergoing clinical development include, for example, INCB024360 (Incyte), indoximod (NewLink Genetics), an IDO peptide vaccine (Copenhagen University), and NLG919 (NewLink Genetics).

EXEMPLIFIED EMBODIMENTS

Embodiment 1

A mesenchymal stem cell (MSC) that is: (a) infected with a naturally occurring or genetically modified oncolytic virus, or (b) is indoleamine 2,3-dioxygenase (IDO)-deficient, or both (a) and (b).

Embodiment 2

The MSC of embodiment 1, wherein the MSC is infected with a naturally occurring or genetically modified oncolytic virus.

Embodiment 3

The MSC of embodiment 1, wherein the MSC is IDO-deficient.

Embodiment 4

The MSC of embodiment 1, wherein the MSC is infected with a naturally occurring or genetically modified oncolytic virus, and wherein the MSC is IDO-deficient.

Embodiment 5

The MSC of any one of embodiments 1 to 4, wherein the oncolytic virus is respiratory syncytial virus (RSV).

Embodiment 6

The MSC of any one of embodiments 1 to 5, wherein the MSC is a human MSC.

Embodiment 7

The MSC of any preceding embodiment, wherein the MSC is rendered IDO-deficient by CRISPR-mediated knockout of IDO.

Embodiment 8

A method for treating cancer, comprising administering an effective amount of the MSC of any one of embodiments 1 to 7 to a human or non-human animal subject in need thereof.

Embodiment 9

The method of embodiment 8, wherein the cancer is lung cancer.

Embodiment 10

The method of embodiment 9, wherein the lung cancer is non-small cell lung cancer (NSCLC).

Embodiment 11

The method of any one of embodiments 8 to 10 further comprising administering an inhibitor of indoleamine 2,3-dioxygenase (IDO inhibitor) to the subject.

Embodiment 12

A method for producing an oncolytic agent, comprising: providing an MSC; and infecting the MSC with an oncolytic virus.

Embodiment 13

The method of embodiment 12, wherein the MSC is indoleamine 2,3-dioxygenase (IDO)-deficient at the time of infection.

Embodiment 14

The method of embodiment 12, further comprising rendering the MSC indoleamine 2,3-dioxygenase (IDO)-deficient before or after said infecting.

Embodiment 15

A method for lysing or inducing apoptosis of cancer cells in vitro or in vivo, comprising contacting the cancer cells in vitro or in vivo with, or bringing into close proximity, an effective amount of MSC of any one of embodiments 1 to 7.

Embodiment 16

The method of embodiment 15, wherein the cancer cells are lung cancer cells.

Embodiment 17

The method of embodiment 16, wherein the lung cancer cells are non-small cell lung cancer (NSCLC).

Embodiment 18

The method of any one of embodiments 15 to 17, further comprising contacting the cancer cells in vitro or in vivo with an inhibitor of indoleamine 2,3-dioxygenase (IDO inhibitor).

Embodiment 19

A composition comprising an MSC of any one of embodiment 1 to 4; and a pharmaceutically acceptable carrier or diluent.

Embodiment 20

The composition of embodiment 19, further comprising an adjuvant.

Further Definitions

The terms "cancer" and "malignancy" are used herein interchangeably to refer to or describe the physiological condition in mammals that is typically characterized by unregulated cell growth. The cancer may be drug-resistant or drug-sensitive. The cancer may be primary or metastatic. The cancer may represent early, middle, or late stage disease, and be acute or chronic. In some embodiments, the cancer is lung cancer. In some embodiments, the cancer is non-small cell lung cancer (NSCLC) or small-cell lung cancer.

Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some embodiments, the cancer is melanoma, MDS, ovarian cancer, breast cancer, or multiple myeloma.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may be treated with the compositions and methods of the invention are listed in Table 2.

TABLE 2

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |

TABLE 2-continued

| Examples of Cancer Types | |
|---|---|
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, Childhood | Oral Cavity Cancer, Lip and Oropharyngeal Cancer |
| Germ Cell Tumor, Extragonadal | Osteosarcoma/Malignant Fibrous Histiocytoma of Bone |
| Germ Cell Tumor, Ovarian | |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and Hypothalamic | Pancreatic Cancer, Childhood |
| | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive Neuroectodermal Tumors, Childhood |
| Soft Tissue Sarcoma, Childhood | |
| Squamous Cell Carcinoma, see Skin Cancer (non-Melanoma) | Pituitary Tumor |
| | Plasma Cell Neoplasm/Multiple Myeloma |
| Squamous Neck Cancer with Occult Primary, Metastatic | Pleuropulmonary Blastoma |
| | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The term "tumor" is inclusive of solid tumors and non-solid tumors.

In the case of cancers, positive clinical outcomes that may result from the methods of the invention that involve treatment include, but are not limited to, alleviation of one or more symptoms of the cancer, diminishment of extent of disease, stabilized (i.e., not worsening) state of disease, delay or slowing of disease progression, amelioration or palliation of the disease state, remission (whether partial or total), whether detectable or undetectable, tumor regression, inhibition of tumor growth, inhibition of tumor metastasis, reduction in cancer cell number, inhibition of cancer cell infiltration into peripheral organs, improved time to disease progression (TTP), improved response rate (RR), prolonged overall survival (OS), prolonged time-to-next-treatment (TNTT), or prolonged time from first progression to next treatment, or a combination of two or more of the foregoing.

The terms "comprising", "consisting of" and "consisting essentially of" are defined according to their standard meaning. The terms may be substituted for one another throughout the instant application in order to attach the specific meaning associated with each term.

The term "effective amount" also means an amount of the agent (e.g., MSC or compositions of the invention) that will elicit the desired biological response within a subject or from a target cancer cell, such as alleviation of one or more symptoms of cancer, or cancer cell lysing or induction of cancer cell apoptosis.

The terms "isolated" or "biologically pure" refer to material that is substantially or essentially free from components which normally accompany the material as it is found in its native state. Thus, MSCs in accordance with the invention preferably do not contain materials normally associated with the MSC in their in situ environment, i.e., are administered in an isolated or purified form. However, the MSCs may be administered to a subject in a non-isolated or non-purified form, e.g., as a tissue.

As used in this specification, the singular forms "a", "an", and "the" include plural reference unless the context clearly dictates otherwise. Thus, for example, a reference to "a cell", e.g., an MSC, includes more than one such cell. A reference to "a compound" includes more than one such compound, and so forth.

Mammalian species which benefit from the disclosed MSC, compositions, and methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient", "subject", and "individual" are used interchangeably and are intended to include such human and non-human species unless specified to be human or non-human.

Subjects in need of treatment using the methods of the present invention (e.g., having a cancer) can be identified using standard techniques known to those in the medical or veterinary professions, as appropriate. A subject having a cancer may be symptomatic or asymptomatic.

Optionally, the MSCs and compositions of the invention may be administered prophylactically to a subject without cancer, to prevent or delay the onset of cancer or its recurrence.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et a. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1. MSCs are Highly Susceptible to RSV Infection.

Figure 1E:
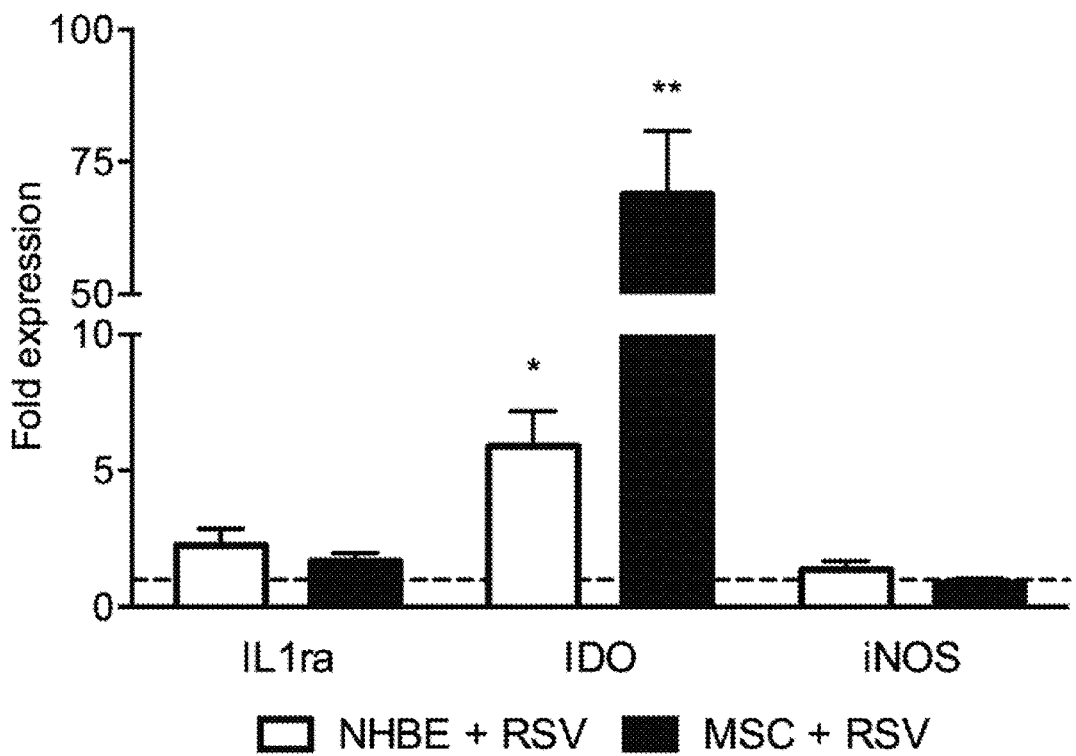

RSV commonly infects the apical airway epithelial cells, but also may infect various immune cells of blood and bone marrow (17-19). An error in cell handling in the inventors' lab led to the finding that human MSCs (hMSCs) are highly susceptible to RSV (FIG. 1). RSV readily and aggressively replicates in MSCs infecting ~90% of cells within 72 h p.i. (FIG. 1 A-C). High expression levels of IFN-β and IDO were found in RSV-infected MSCs compared to mock (FIG. 1D-E). Also, these cells exhibit expression of IL-1β, IL-6, IL-8, prostaglandin D2 (PGD2) and CXCR4, (not shown).

Example 2. IDO Deficient MSCs are Equally Susceptible to RSV Infection.

Figure 2D:
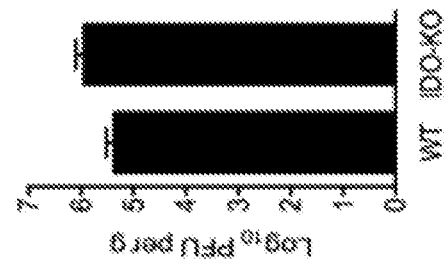
Figure 2E:
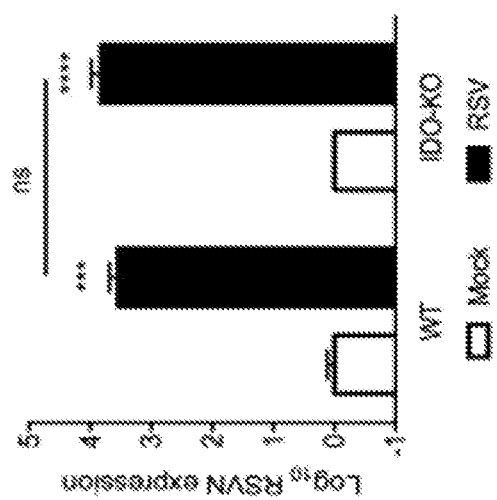
Figure 2F:
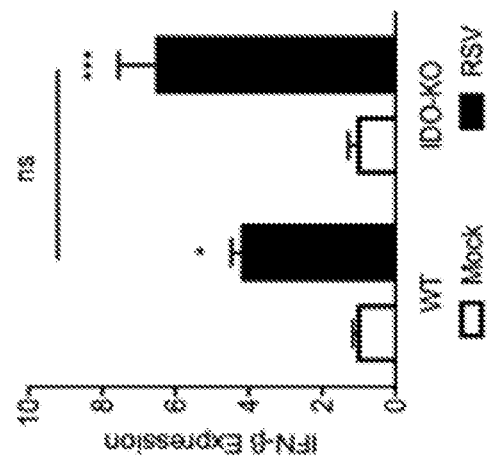

To examine the immunological consequences of RSV-infected MSCs, the inventors isolated fresh human peripheral blood mononuclear cells (PBMCs) and treated them with conditioned medium (CM) from MSCs. PBMCs were stained with 5,6-carboxyfluorescein diacetate succinimidyl ester (CFSE) and treated with CM collected from the MSC culture infected with RSV in the presence or absence of IDO inhibitors, 1-methyltryptophan (1-MT) and vitamin $K_3$. As expected, IDO secreted in the MSC culture supernatant inhibited lymphocyte proliferation (FIG. 2A) whereas treatment of RSV-infected MSCs with 1-MT or vitamin $K_3$ reduced kynurenine levels (FIG. 2C) and abolished the negative effect on PBMC proliferation measured by CFSE dye dilution by flow cytometry (FIG. 2A). However, 1-MT or vitamin $K_3$ treatment did not reduce RSV infection as determined by viral titers (FIG. 2B). The inventors also examined the susceptibility of wt and IDO knockout mice to RSV infection. RSV infected and replicated in wt and IDO knockout mice and there was no statistical difference in the numbers of PFUs or RSV nucleocapsid (RSVN) transcript (FIG. 2E) or IFN-β transcript (FIG. 2F) found in the lungs of wt versus IDO-knockout mice.

Example 3. CRISPR-Mediated Knockout of IDO Prevents Anti-Proliferative Effects of RSV-Infected MSCs but Retained Susceptibility to RSV Infection.

Figure 3A:
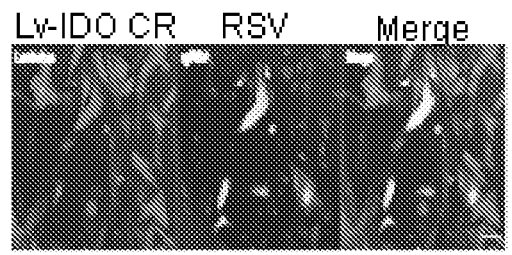
FIGS. 3A-3C: IDO-deficient hMSCs remained susceptible to RSV infection. Human MSCs were transduced with lentiviral (Lv) particles containing the pCRISPR-LvSG03 expression plasmid for mCherry, CRISPR associated protein 9 (Cas9), and one of two human IDO-specific single guide (sg) RNAs (LvA and LvB) or a scrambled control (LvS) (GeneCopoeia) in the presence of 10 μg per mL polybrene for 12 hours, per manufacturer's instructions. The cells were incubated for 48 hours prior to infection with rgRSV. (3A) Lentiviral transduction and RSV infection were visualized by fluorescent microscopy for mCherry (red) and GFP (green) respectively. (3B) Knockout of IDO eliminates the immune regulatory effect of RSV-infected MSCs. Proliferation of PBMCs treated with conditioned media from MSCs was detected by CFSE, n=3, $**p<0.0001$ vs. PHA control, $\ddagger p<0.0001$ vs. LvS. (3C) RSV infection quantified by real-time PCR (I) $*p<0.05$ vs. LvS-R.
Figure 3B:
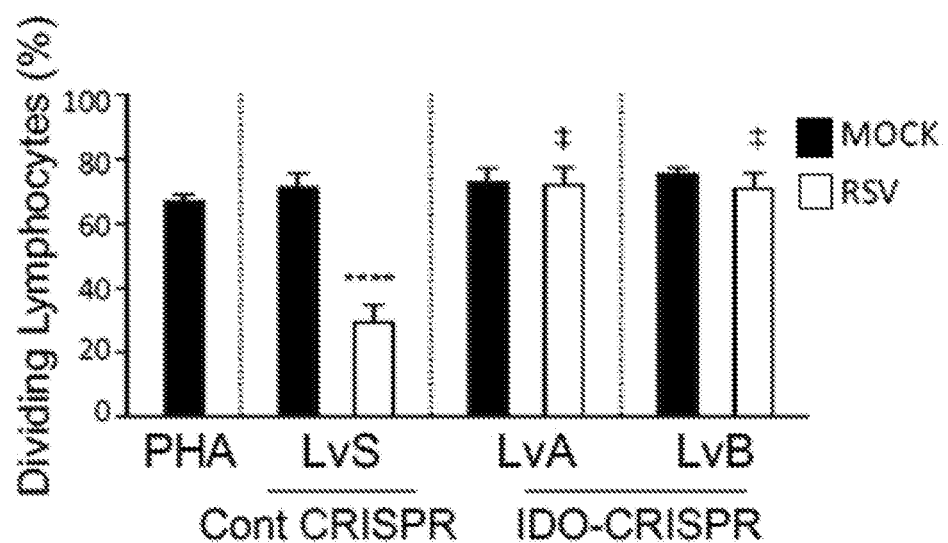
Figure 3C:
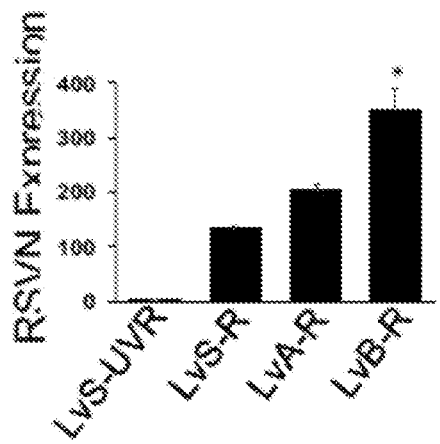

As an alternative method to the use of IDO inhibitors, which may have off-target effects, the inventors utilized the CRISPR/Cas9 system to knockout the IDO gene from the hMSCs prior to infection with RSV. Two separate plasmids expressing different IDO-specific guide RNAs (LvA and LvB) as well as a control plasmid expressing a non-targeted scrambled guide RNA (LvS) (GeneCopoeia) were transfected individually into hMSCs. Expression of the plasmid was evident by fluorescent microscopy for mCherry (red) in cells (FIG. 3A). Similarly, infection with rgRSV was observed by GFP (green) fluorescence (FIG. 3A). Conditioned media from IDO-knockout and control hMSCs was used in to treat PBMCs during a CFSE proliferation assay, as described in FIG. 2A. Media from control hMSCs (LvS) resulted in a similar reduction in PBMC proliferation as had been seen in FIG. 2A, however PBMC treatment with media from each of the two IDO-knockout constructs (LvA and LvB) showed no RSV-associated reduction in proliferation (FIG. 3B), suggesting that these hMSCs lacked IDO expression. However, IDO-deficient hMSCs retained their susceptibility to RSV infection (FIG. 3C).

Example 4. IDO Inhibitor does not Affect hMSC Migration.

To test the effect of 1-MT on the migratory capacity of hMSCs the inventors used a Boyden chamber invasion assay with Lewis lung carcinoma (LLC1) cells in the bottom chamber to produce trophic factors. MSCs were seeded on the top of a matrigel layer above a PET membrane with 8.0 μm pores (BD Bioscience) and treated with control MSC media or media containing 1MT. Cells were cocultured for 24 hours before fixation in 4% paraformaldehyde in PBS. Upper matrigel layer was removed by cue tip and migrant cells were visualized and counted by Giemsa staining. Results shown in FIG. 4 suggest that IDO inhibitor did not inhibit migration of hMSC towards LLC1 cells.

Example 5. RSV Infection in LLC1 Cells In Vitro and In Vivo.

Figure 5D:
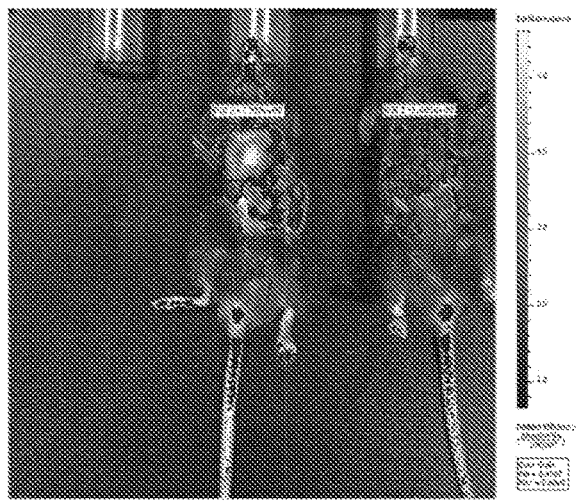
Figure 5E:
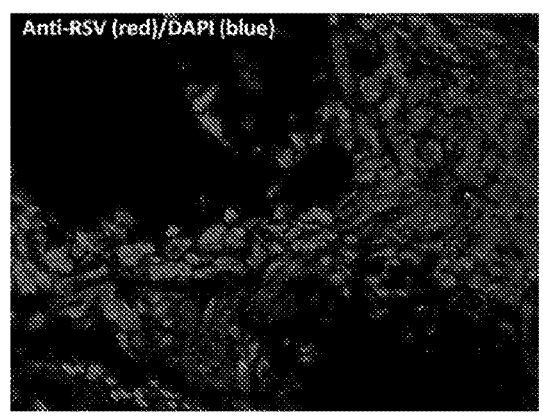
Figure 5F:
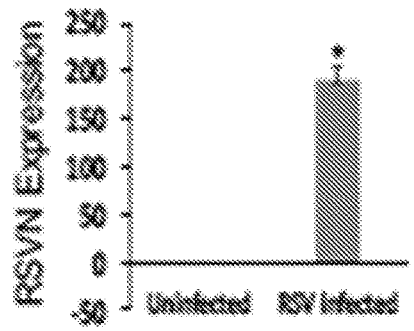

LLC1 cells were infected with 1 and 5 MOI of rA2-KL19F strain expressing a red fluorescent marker, mKate2 (14), and cells were examined using fluorescent microscope. Forty-eight hrs after infection, majority of cells were found to be infected with RSV (FIG. 5A). The inventors further examined the potential of conditioned medium of RSV-infected hMSCs (FIG. 2) to infect LLC1 tumoroids. LLC1 tumoroids were cultured in the presence of conditioned medium of rgRSV-infected MSCs for 90 mins and cells were examined 72 hrs after infection by confocal microscopy. Results show that LLC1 tumoroids were readily infected by rgRSV (FIG. 5B), suggesting the potential of this platform to screen oncolytic potential of genetically engineered RSV ex vivo. hMSCs are known to have tumor tropism. Further, tumor tropism of human MSCs to mouse tumors have been demonstrated before (20). Consistent with this, RSV-loaded hMSCs when administered intranasally or i.v. (FIG. 5D) homed to the lungs of tumor bearing (orthotopic LLC1 inoculated) C57BL/6 mouse (FIG. 5C). Moreover, RSV-loaded hMSCs when administered intranasally to LLC1 tumor bearing mice, hMSC survived and RSV replicated in the tumor cells (FIG. 5E-F).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Schild S E, Tan A D, Wampfler J A, et al. A new scoring system for predicting survival in patients with non-small cell lung cancer. Cancer medicine. 2015. doi: 10.1002/cam4.479. PubMed PMID: 26108458.
2. Bradley J D, Paulus R, Graham M V, et al. Phase II trial of postoperative adjuvant paclitaxel/carboplatin and thoracic radiotherapy in resected stage II and IIIA non-smallcell lung cancer: promising long-term results of the Radiation Therapy Oncology Group—RTOG 9705. J Clin Oncol. 2005; 23(15):3480-7. PubMed PMID: 15908657.
3. Biard D S, Martin M, Rhun Y L, et al. Concomitant p53 gene mutation and increased radiosensitivity in rat lung embryo epithelial cells during neoplastic development. Cancer Res. 1994; 54(13):3361-4. PubMed PMID: 8012950.
4. Wang H, Yu J M, Yang G R, et al. Further characterization of the epidermal growth factor receptor ligand 11C-PD153035. Chinese medical journal. 2007; 120(11):960-4. PubMed PMID: 17624262.
5. Xu Q Y, Gao Y, Liu Y, et al. Identification of differential gene expression profiles of radioresistant lung cancer cell line established by fractionated ionizing radiation in vitro. Chinese medical journal. 2008; 121(18): 1830-7. PubMed PMID: 19080366.
6. Jones G C, Kehrer J D, Kahn J, et al. Primary Treatment Options for High-Risk/Medically Inoperable Early Stage NSCLC Patients. Clin Lung Cancer. 2015; 16(6):413-30. doi: 10.1016/j.cllc.2015.04.001. PubMed PMID: 26027433; PubMed Central PMCID: PMCPMC4609584.
7. Russell S J, Peng K W, Bell J C. Oncolytic virotherapy. Nature biotechnology. 2012; 30(7):658-70. doi: 10.1038/nbt.2287. PubMed PMID: 22781695; PubMed Central PMCID: PMC3888062.
8. Donnelly O G, Errington-Mais F, Prestwich R, et al. Recent clinical experience with oncolytic viruses. Current pharmaceutical biotechnology. 2012; 13(9):1834-41. PubMed PMID: 21740364.
9. Ferguson M S, Lemoine N R, Wang Y. Systemic delivery of oncolytic viruses: hopes and hurdles. Advances in virology. 2012; 2012:805629. doi: 10.1155/2012/805629. PubMed PMID: 22400027; PubMed Central PMCID: PMC3287020.
10. Ikeda K, Ichikawa T, Wakimoto H, et al. Oncolytic virus therapy of multiple tumors in the brain requires suppression of innate and elicited antiviral responses. Nature medicine. 1999; 5(8):881-7. doi: 10.1038/11320. PubMed PMID: 10426310.
11. Bird G H, Boyapalle S, Wong T, et al. Mucosal delivery of a double-stapled RSV peptide prevents nasopulmonary infection. The Journal of clinical investigation. 2014; 124(5):2113-24. doi: 10.1172/JCI71856. PubMed PMID: 24743147; PubMed Central PMCID: PMC4001541.
12. Wong T M, Boyapalle S, Sampayo V, et al. Respiratory syncytial virus (RSV) infection in elderly mice results in altered antiviral gene expression and enhanced pathology.

13. Boyapalle S, Wong T, Garay J, et al. Respiratory syncytial virus NS1 protein colocalizes with mitochondrial antiviral signaling protein MAVS following infection. PloS one. 2012; 7(2):e29386. doi: 10.1371/journal.pone.0029386. PubMed PMID: 22383950; PubMed Central PMCID: PMC3288005.
14. Zhang W, Yang H, Kong X, et al. Inhibition of respiratory syncytial virus infection with intranasal siRNA nanoparticles targeting the viral NS1 gene. Nature medicine. 2005; 11(1):56-62. doi: 10.1038/nm1174. PubMed PMID: 15619625.
15. Echchgadda I, Chang T H, Sabbah A, et al. Oncolytic targeting of androgen-sensitive prostate tumor by the respiratory syncytial virus (RSV): consequences of deficient interferon-dependent antiviral defense. BMC cancer. 2011; 11:43. doi: 10.1186/1471-2407-11-43. PubMed PMID: 21276246; PubMed Central PMCID: PMC3038980.
16. Guerrero-Plata A, Baron S, Poast J S, et al. Activity and regulation of alpha interferon in respiratory syncytial virus and human metapneumovirus experimental infections. Journal of virology. 2005; 79(16): 10190-9. doi: 10.1128/JVI.79.16.10190-10199.2005. PubMed PMID: 16051812; PubMed Central PMCID: PMC1182647.
17. Hobson L, Everard M L. Persistent of respiratory syncytial virus in human dendritic cells and influence of nitric oxide. Clinical and experimental immunology. 2008; 151 (2):359-66. Epub 2007/12/08. doi: 10.1111/j.1365-2249.2007.03560.x. PubMed PMID: 18062796; PubMed Central PMCID: PMC2276949.
18. Ajamian F, Wu Y, Davoine F, et al. Respiratory syncytial virus replication induces Indoleamine 2, 3-dioxygenase (IDO) activation in human dendritic cells. Allergy, Asthma & Clinical Immunology. 2010; 6:1-2.
19. Rezaee F, Gibson L F, Piktel D, et al. Respiratory syncytial virus infection in human bone marrow stromal cells. Am J Respir Cell Mol Biol. 2011; 45(2):277-86. doi: 10.1165/rcmb.2010-0121OC. PubMed PMID: 20971883; PubMed Central PMCID: PMC3175557.
20. Jing W, Chen Y, Lu L, et al. Human umbilical cord blood-derived mesenchymal stem cells producing IL15 eradicate established pancreatic tumor in syngeneic mice. Mol Cancer Ther. 2014; 13(8):2127-37. doi: 10.1158/1535-7163.MCT-14-0175. PubMed PMID: 24928851.
21. Moon Y W, J Hajjar, P Hwu, et al. Targeting the indoleamine 2,3-dioxygenase pathway in cancer. Journal for ImmunoTherapy of Cancer. 2015; 3:41. Doi: 10.1186/s40425-015-0094-9.
22. Unniyampurath U, R Pilankatta, and M Krishnan. RNA Interference in the Age of CRISPR: Will CRISPR Interfere with RNAi? International Journal of Molecular Sciences. 2016; 17:291. Doi:10.3390/ijms17030291.
23. Boettcher M and MT McManus. Mol Cell. 2015; 58(4): 575-585. Doi: 10.1016/j.molcel.2015.04.028.
24. David E. Knockout by TALEN or CRISPR vs. Knockdown by shRNA or siRNA. GeneCopoeia Technical Note. Downloaded from genecopoeia.com on Sep. 19, 2017.

We claim:

1. A mesenchymal stem cell (MSC) that is indoleamine 2,3-dioxygenase (IDO)-deficient due to CRISPR-mediated knockout of IDO and over-expresses interferon-beta.

2. The MSC of claim 1, wherein the MSC is a human MSC.

3. A method for treating cancer, comprising administering an effective amount of the MSC of claim 1 to a human or non-human animal subject in need thereof.

4. The method of claim 3, wherein the cancer is lung cancer.

5. The method of claim 4, wherein the lung cancer is non-small cell lung cancer (NSCLC).

6. The method of claim 3, further comprising administering an inhibitor of indoleamine 2,3-dioxygenase (IDO inhibitor) to the subject.

7. The method of claim 6, wherein the IDO inhibitor comprises a small molecule, or a biologic molecule selected from among a nucleic acid, protein, peptide, antibody, or antibody fragment.

8. The method of claim 7, wherein the IDO inhibitor comprises an IDO peptide vaccine or NLG919.

9. The method of claim 6, wherein the IDO inhibitor comprises a hydroxyamidine or tryptophan analog.

10. A method for lysing or inducing apoptosis of cancer cells in vitro or in vivo, comprising contacting the cancer cells in vitro or in vivo with, or bringing into close proximity, an effective amount of MSC of claim 1.

11. The method of claim 10, wherein the cancer cells are lung cancer cells.

12. The method of claim 11, wherein the lung cancer cells are non-small cell lung cancer (NSCLC).

13. The method of claim 10, further comprising contacting the cancer cells in vitro or in vivo with an inhibitor of indoleamine 2,3-dioxygenase (IDO inhibitor).

14. A composition comprising an MSC of claim 1; and a pharmaceutically acceptable carrier or diluent.

15. The composition of claim 14, further comprising an adjuvant.

* * * * *